United States Patent [19]

Marquis et al.

[11] Patent Number: 5,053,569

[45] Date of Patent: Oct. 1, 1991

[54] PROCESS FOR OLIGOMERIZING OLEFINS TO PREPARE BASE STOCKS FOR SYNTHETIC LUBRICANTS

[75] Inventors: Edward T. Marquis, Austin; John R. Sanderson, Leander; John F. Knifton, Austin, all of Tex.

[73] Assignee: Texaco Chemical Company, White Plains, N.Y.

[21] Appl. No.: 500,631

[22] Filed: Mar. 28, 1990

[51] Int. Cl.$^5$ ............................................. C07C 2/02
[52] U.S. Cl. .................................. 585/255; 585/533; 585/18
[58] Field of Search ........................ 585/18, 255, 533

[56] References Cited

U.S. PATENT DOCUMENTS

| | | | |
|---|---|---|---|
| 1,919,722 | 7/1933 | Hyman | 585/533 |
| 2,543,016 | 2/1951 | Grosse | 585/255 |
| 2,574,895 | 11/1951 | Stecker | 585/533 |
| 2,951,087 | 8/1960 | Hauser et al. | 502/62 |
| 3,412,039 | 11/1968 | Miller | 252/428 |
| 3,432,571 | 3/1969 | Noddings et al. | 260/641 |
| 3,459,815 | 8/1969 | Noddings et al. | 260/641 |
| 3,845,150 | 10/1974 | Yan et al. | 260/673.5 |
| 3,849,507 | 11/1974 | Zuech | 260/671 C |
| 4,153,638 | 5/1979 | Bercik et al. | 585/526 |
| 4,299,730 | 11/1981 | Sommer et al. | 252/435 |
| 4,329,257 | 5/1982 | Sommer et al. | 252/435 |
| 4,351,980 | 9/1982 | Reusser et al. | 585/820 |
| 4,456,779 | 6/1984 | Owen et al. | 585/415 |
| 4,480,142 | 10/1984 | Cobb | 585/464 |
| 4,531,014 | 7/1985 | Gregory et al. | 585/415 |
| 4,604,491 | 8/1986 | Dressler et al. | |
| 4,827,064 | 5/1989 | Wu | 585/530 |
| 4,879,425 | 11/1989 | Kukes et al. | 585/350 |

OTHER PUBLICATIONS

"Synthetic Lubricants from Internal Olefins", Process Evaluation/Research Planning Report by Chem Systems, 84-Q-1, pp. 17-45.
Figueras, "Pillared Clays as Catalysts", Catal. Rev.-Sci. Eng. 30(3), pp. 457-499 (1988).
Friedlander, "Organized Polymerization, I. Olefins on a Clay Surface", Journal of Polymer Science, Part C, No. 4, pp. 1291-1301.
Friedlander et al., "Organized Polymerization III. Monomers Intercalated in Montmorillonite", Polymer Letters, vol. 2, pp. 475-479 (1964).
"Intercalated Catalysts and Pillared Clays", from a Process Evaluation/Research Planning Report by Chem Systems titled, Catalysts: Selected Developments, 84-3, pp. 239-249 (Dec. 1985).
Bolan, "Synthetic Lubricant Base Stocks", Process Economics Program Report, No. 125 by SRI International, Apr. 1989.
Bolan, "Synthetic Lubricant Base Stocks", Supplement A, Process Economics Program Report No. 125 by SRI International, Sept. 1989.
Kuliev et al., "Preparation of High-Viscosity Synthetic Lubricants Using an Aluminosilicate Catalyst", Institute of Petrochemical Processes of *Azerbaidzhan SSR, Azerbaidzhanskoe, Neftiano*, Khoziaistvo, 1983, No. 4, pp. 40-43.
Adams in "Synthetic Organic Chemistry Using Pillared, Cation-Exchanged and Acid-Treated Montmorillonite Catalysts—A Review", *Applied Clay Science*, 2 (1987), pp. 304-342.
Adams et al. in "Clays as Selective Catalysts in Organic Synthesis", *Journal of Inclusion Phenomena*, vol. 5 (1987), pp. 663-674.
Chauduri and Sharma, "Some Novel Aspects of the Dimerization of α-Methylstyrene with Acidic Ion-Exchange Resins, Clays, and Other Acidic Materials as Catalysts", Ind. Eng. Res., vol. 28, pp. 1757-1763 (1989).
Purnell, "Catalysis by Ion-Exchanged Montmorillonites", *Catalysis Letters*, 5 (1990), pp. 203-210.

*Primary Examiner*—Patrick P. Garvin
*Assistant Examiner*—E. D. Irzinski
*Attorney, Agent, or Firm*—Jack H. Park; Kenneth R. Priem; Russell R. Stolle

[57] ABSTRACT

A process is disclosed for preparing synthetic lubricant base stocks. Synthetic lubricant base stocks may be prepared in good yield by oligomerizing linear olefins using certain acidic calcium montmorillonite clay catalysts. When the oligomers are hydrogenated, they provide a synthetic lubricant base stock having excellent properties.

35 Claims, No Drawings

PROCESS FOR OLIGOMERIZING OLEFINS TO PREPARE BASE STOCKS FOR SYNTHETIC LUBRICANTS

BACKGROUND OF THE INVENTION 1. Field of the Invention

The invention relates to the preparation of synthetic lubricant base stocks, and more particularly to synthetic lubricant base stocks made by oligomerizing linear olefins by means of certain acidic montmorillonite clay catalysts. 2. Description of Related Methods Synthetic lubricants are prepared from man-made base stocks having uniform molecular structures and, therefore, well-defined properties that can be tailored to specific applications. Mineral oil base stocks, on the other hand, are prepared from crude oil and consist of complex mixtures of naturally occurring hydrocarbons. The higher degree of uniformity found in synthetic lubricants generally results in superior performance properties. For example, synthetic lubricants are characterized by excellent thermal stability. As automobile engines are reduced in size to save weight and fuel, they run at higher termperatures, therefore requiring a more thermally stable oil. Because lubricants made from synthetic base stocks have such properties as excellent oxidative/thermal stability, very low volatility, and good viscosity indices over a wide range of temperatures, they offer better lubrication and permit longer drain intervals, with less oil vaporization loss between oil changes.

Synthetic base stocks may be prepared by oligomerizing internal and alpha-olefin monomers to form a mixture of dimers, trimers, tetramers, and pentamers, with minimal amounts of higher oligomers. The unsaturated oligomer products are then hydrogenated to improve their oxidative stability. The resulting synthetic base stocks have uniform isoparaffinic hydrocarbon structures similar to high quality paraffinic mineral base stocks, but have the superior properties mentioned due to their higher degree of uniformity.

Synthetic base stocks are produced in a broad range of viscosity grades. It is common practice to classify the base stocks by their viscosities, measured in centistokes (cSt) at 100° C. Those base stocks with viscosities less than or equal to about 4 cSt are commonly referred to as "low viscosity" base stocks, whereas base stocks having a viscosity in the range of around 40 to 100 cSt are commonly referred to as "high viscosity" base stocks. Base stocks having a viscosity of about 4 to about 8 cSt are referred to as "medium viscosity" base stocks. The low viscosity base stocks generally are recommended for low temperature applications. Higher temperature applications, such as motor oils, automatic transmission fluids, turbine lubricants, and other industrial lubricants, generally require higher viscosities, such as those provided by medium viscosity base stocks (i.e. 4 to 8 cSt grades). High viscosity base stocks are used in gear oils and as blending stocks.

The viscosity of the base stocks is determined by the length of the oligomer molecules formed during the oligomerization reaction. The degree of oligomerization is affected by the catalyst and reaction conditions employed during the oligomerization reaction. The length of the carbon chain of the monomer starting material also has a direct influence on the properties of the oligomer products. Fluids prepared from short-chain monomers tend to have low pour points and moderately low viscosity indices, whereas fluids prepared from long-chain monomers tend to have moderately low pour points and higher viscosity indices. Oligomers prepared from long-chain monomers generally are more suitable than those prepared from shorter-chain monomers for use as medium viscosity synthetic lubricant base stocks.

One known approach to oligomerizing long-chain olefins to prepare synthetic lubricant base stocks is to contact the olefin with boron trifluoride together with a promotor at a reaction temperature sufficient to effect oligomerization of the olefin. See, for example, co-assigned U.S. Pat. Nos. 4,400,565; 4,420,646; 4,420,647; and 4,434,308. However, boron trifluoride gas ($BF_3$) is a pulmonary irritant, and breathing the gas or fumes formed by hydration of the gas with atmospheric moisture poses hazards preferably avoided. Additionally, the disposal/neutralization of $BF_3$ raises environmental concerns. Thus, a method for oligomerizing long-chain olefins using a non-hazardous, non-polluting catalyst would be a substantial improvement in the art.

Kuliev et al. attempted to prepare synthetic lubricants by oligomerizing long-chain ($C_9$–$C_{14}$) olefins using non-hazardous and non-polluting acidic clays comprising sulfuric and hydrochloric acid-activated bentonites from the Azerbaidzhan SSR. See Kuliev, Abasova, Gasanova, Kotlyarevskaya, and Valiev, "Preparation of High-Viscosity Synthetic Lubricants Using an Aluminosilicate Catalyst," Institute of Petrochemical Processes of the Academy of Sciences of the Azerbaidzhan SSR, Azer. Neft. Khoz., 1983, No. 4, pages 40–43. However, Kuliev et al. concluded that "it was not possible to prepare viscous or high-viscosity oils by olefin polymerization over an aluminosilicate catalyst" and that "hydrogen redistribution reactions predominate with formation of aromatic hydrocarbon, coke, and paraffinic hydrocarbon." Gregory et al., on the other hand, used Wyoming bentonite to oligomerize shorter-chain olefins. (See U.S. Pat. No. 4,531,014.) However, like Kuliev et al., they also were unable to obtain a product high in dimer, trimer and tetramer, and low in disproportionation products.

Surprisingly, Applicants have discovered that it is possible to prepare synthetic lubricant base stocks in good yield by oligomerizing long-chain olefins using certain acidic montmorillonite clay catalysts. Applicants have found that a high conversion of long-chain olefin to dimer, trimer, and tetramer may be obtained with formation of very little concomitant hydrogen redistribution by-product by using an acidic calcium montmorillonite clay having a moisture content ranging up to about 20 wt. %, a residual acidity in the range of about 3 to about 30 mg KOH/g (when titrated to a phenolphthalein end point), and a surface area of about 300 $M^2$/g or greater. In addition to being excellent catalysts, these clays are non-hazardous and non-polluting.

SUMMARY OF THE INVENTION

The invention relates to a process for the preparation of oligomers, comprising contacting a linear olefin containing at least 10 carbon atoms with a catalyst comprising an acidic calcium montmorillonite clay having a moisture content ranging up to about 20 wt. %, a residual acidity in the range of about 3 to about 30 mg KOH/g (when titrated to a phenolphthalein end point), and a surface area of about 300 $M^2$/g or greater.

DESCRIPTION OF THE PREFERRED EMBODIMENTS

Applicants have discovered that synthetic lubricant base stocks may be prepared in good yield by oligomerizing long-chain olefins using certain acidic montmorillonite clay catalysts. The olefin monomer feed stocks used in the present invention may be selected from compounds comprising (1) alpha-olefins having the formula $R''CH=CH_2$, where $R''$ is an alkyl radical of 8 to 22 carbon atoms, and (2) internal olefins having the formula $RCH=CHR'$, where R and R' are the same or different alkyl radicals of 1 to 20 carbon atoms, provided that the total number of carbon atoms in any one olefin shall be within the range of 10 to 24, inclusive. A preferred range for the total number of carbon atoms in any one olefin molecule is 12 to 18, inclusive, with an especially preferred range being 13 to 16, inclusive. Mixtures of internal and alpha-olefins may be used, as well as mixtures of olefins having different numbers of carbon atoms, provided that the total number of carbon atoms in any one olefin shall be within the range of 10 to 24, inclusive. The alpha and internal-olefins to be oligomerized in this invention may be obtained by processes well-known to those skilled in the art and are commercially available.

The oligomerization reaction may be represented by the following general equation:

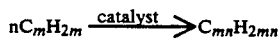

where n represents moles of monomer and m represents the number of carbon atoms in the monomer. Thus, the oligomerization of 1-decene may be represented as follows:

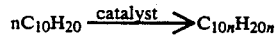

The reaction occurs sequentially. Initially, olefin monomer reacts with olefin monomer to form dimers. The dimers that are formed then react with additional olefin monomer to form trimers, and so on. This results in an oligomer product distribution that varies with reaction time. As the reaction time increases, the olefin monomer conversion increases, and the selectivities for the heavier oligomers increase. Generally, each resulting oligomer contains one double bond.

The catalysts used to effect this reaction in the present invention are certain silica-alumina clays, also called aluminosilicates. Silica-alumina clays primarily are composed of silicon, aluminum, and oxygen, with minor amounts of magnesium and iron in some cases. Variations in the ratios of these constituents, and in their crystal lattice configurations, result in some fifty separate clays, each with its own characteristic properties.

One class of silica-alumina clays comprises smectite clays. Smectite clays have a small particle size and unusual intercalation properties which afford them a high surface area. Smectites comprise layered sheets of octahedral sites between sheets of tetrahedral sites, where the distance between the layers can be adjusted by swelling, using an appropriate solvent. Three-layered sheet-type smectites include montmorillonites. The montmorillonite structure may be represented by the following formula:

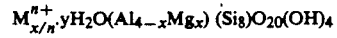

where M represents the interlamellar (balancing) cations, normally sodium or lithium; and x, y and n are integers.

Montmorillonite clays may be acid-activated by such mineral acids as sulfuric acid and hydrochloric acid. Mineral acids activate montmorillonites by attacking and solubilizing structural cations in the octahedral layers. This opens up the clay structure and increases surface area. These acid-treated clays act as strong Bronsted acids. Applicants have discovered that certain acid-treated montmorillonite clay catalysts are particularly effective for preparing synthetic lubricant base stocks in good yield by oligomerizing long-chain olefins. These clays are acidic calcium montmorillonite clays having a moisture content ranging up to about 20 wt. %, a residual acidity in the range of about 3 to about 30 mg KOH/g (when titrated to a phenolphthalein end point), and a surface area of about 300 $M^2$/g or greater. Illustrative examples include Filtrol grade 24, having a moisture content of 12 wt. %, a residual acidity of 8.5 mg KOH/g, and a surface area of 425 $M^2$/g; Filtrol grade 124, having a moisture content of 2 wt. %, a residual acidity of 7.0 mg KOH/g, and a surface area of 400 $M^2$/g; Filtrol grade 13, having a moisture content of 16 wt. %, a residual acidity of 15 mg KOH/g, and a surface area of 300 $M^2$/g; Filtrol grade 113, having a moisture content of 4 wt. %, a residual acidity of 10 mg KOH/g, and a surface area of 300 $M^2$/g; and Filtrol grade 224, having virtually no moisture, and having a residual acidity of 3.0 mg KOH/g, and a surface area of 350 $M^2$/g.

Preferably, the catalyst is activated by heat treatment before running the reaction. Applicants have found, surprisingly, that heat treatment of the catalyst prior to running the oligomerization reaction causes the catalyst to be more active and produce a higher olefin conversion. Additionally, clays heat treated in this manner are more stable, remaining active during the oligomerization reaction for a longer period of time. The clays may be heat treated at temperatures in the range of about 50° to 400° C., with or without the use of a vacuum. A more preferred temperature range is 50° to 300° C. Optionally, an inert gas may be used during heat treatment as well. Preferably, the clay should be heat treated under conditions and for a length of time which will reduce the water content of the clay to approximately 1 wt. % or less.

The oligomerization reaction may be carried out in either a stirred slurry reactor or in a fixed bed continuous flow reactor. The catalyst concentration should be sufficient to provide the desired catalytic effect. The temperatures at which the oligomerization may be performed are between about 50° and 300° C., with the preferred range being about 150° to 180° C. The reaction may be run at pressures of from 0 to 1000 psig.

Following the oligomerization reaction, the unsaturated oligomers may be hydrogenated to improve their thermal stability and to guard against oxidative degradation during their use as lubricants. The hydrogenation reaction for 1-decene oligomers may be represented as follows:

where n represents moles of monomer used to form the oligomer. Hydrogenation processes known to those skilled in the art may be used to hydrogenate the oligomers. A number of metal catalysts are suitable for promoting the hydrogenation reaction, including nickel, platinum, palladium, copper, and Raney nickel. These metals may be supported on a variety of porous materials such as kieselguhr, alumina, or charcoal. A particularly preferred catalyst for this hydrogenation is a nickel-copper-chromia catalyst described in U.S. Pat. No. 3,152,998, incorporated by reference herein. Other U.S. patents disclosing known hydrogenation procedures include U.S. Pat. Nos. 4,045,508; 4,013,736; 3,997,622; and 3,997,621.

While it is known to include a distillation step after the hydrogenation procedure to obtain products of various 100° C. viscosities, it is preferred in the method of the present invention that no further distillation (beyond monomer flashing) be conducted. In other words, the monomer-stripped, hydrogenated bottoms are the desired synthetic lubricant components. Thus, the method of this invention does not require the costly, customary distillation step, yet, surprisingly, produces a synthetic lubricant component that has excellent properties and that performs in a superior fashion. However, in some contexts, one skilled in the art may find subsequent distillation useful in the practice of this invention.

The monomer stripping step should be conducted under mild conditions. Distillation at temperatures exceeding 210° C. may cause the oligomers to break down in some fashion and come off as volatiles. Preferably, therefore, the reboiler or pot temperature should be kept at or under about 180° C. when stripping out the monomer.

The invention will be further illustrated by the following examples, which are given by way of illustration and not as limitations on the scope of this invention.

EXAMPLE I

The following demonstrates the use of the present invention in batch reaction systems:

Batch-Flask

Olefin and clay catalyst were charged to a flask equipped with a stirrer, thermometer, heating mantle, and a water-cooled condenser ($N_2$ purge). The mixture was vigorously stirred and heated to a desired temperature for the desired time. The mixture was then cooled to ambient temperature and filtered with suction. The liquid was analyzed by liquid chromatography. The results are detailed in Table I.

Batch-Autoclave

Olefin and clay catalyst were charged to an autoclave. The autoclave was sealed and heated to the desired temperature for the desired time. The mixture was then cooled to ambient temperature and filtered with suction. The liquid was then analyzed by liquid chromatography. The results are shown in Table I.

Hydrogenation of Oligomer

An autoclave was charged with oligomer prepared in Batch No. 6 of Table I and finely powdered nickel catalyst. The autoclave was flushed with hydrogen and then pressured to 1000 psig with hydrogen. The mixture was heated to 200° C. and stirred at this temperature for 4 hours. The mixture was then repressured with hydrogen to 2000 psig as needed. The mixture was then cooled to ambient temperature, the catalyst was filtered and the monomer was removed. Typical results are shown in Table II.

TABLE I

| OLEFIN OLIGOMERIZATION WITH ACIDIC CLAYS (BATCH REACTIONS) | | | | | |
| --- | --- | --- | --- | --- | --- |
| Batch No. | Olefin(s) (by carbon number) | (g) | Harshaw/Filtrol Catalyst | (g) | Reactor |
| 1 | C-14A | 101 | H/F Clay 13 | 25 | Flask |
| 2 | C-14A | 100 | H/F Clay 24 | 25 | Flask |
| 3 | C-14A | 100 | H/F Clay 13 | 10 | Clave |
| 4 | C-14A | 100 | H/F Clay 24 | 10 | Clave |
| 5 | C-14A | 100 | 85% $H_3PO_4$ | 10 | Clave |
| 6 | C-14A | 350 | H/F Clay 24 | 50 | Flask |
| 7 | C-13I, 14I (40%, 60%) | 350 | H/F Clay 24 | 50 | Flask |
| 8 | C-13I, 14I C-14A | 250 100 | H/F Clay 24 | 50 | Flask |
| 9 | C-13I, 14I (40%, 60%) | 350 | H/F Clay 24 | 50 | Flask |
| 10 | C-15I, 16I | 350 | H/F Clay 24 | 50 | Flask |
| 11 | C-15I, 16I | 350 | H/F Clay 24 | 50 | Flask |
| 12 | C-14A, 16A (63%, 36%) | 350 | H/F Clay 24 | 50 | Flask |
| 13 | C-14A, 16A (63%, 36%) | 400 | H/F Clay 24 | 20 | Flask |
| 14 | C-14A, 16A (63%, 36%) | 400 | H/F Clay 24 | 10 | Flask |
| 15 | C-14A, 16A (63%, 36%) | 400 | H/F Clay 24 | 40 | Flask |

| Batch No. | Time/Temp (Hr)/(°C.) | Con. (%) | M (%) | D (%) | T+ (%) | D/T + Ratio |
| --- | --- | --- | --- | --- | --- | --- |
| 1 | 3/150 | 81.9 | 18.1 | 49.1 | 32.8 | 1.50 |
| 2 | 4/150 | 92.4 | 7.6 | 43.9 | 48.4 | 0.91 |
| 3 | 4/300 | 78.9 | 21.1 | 55.3 | 23.4 | 2.36 |
| 4 | 4/300 | 57.6 | 42.4 | 46.4 | 11.2 | 4.14 |
| 5 | 4/300 | 15.6 | 84.4 | 7.87 | 7.69 | 1.02 |
| 6 | 4/150 | 80.0 | 20.0 | 49.0 | 31.0 | 1.58 |

TABLE I-continued
OLEFIN OLIGOMERIZATION WITH ACIDIC CLAYS
(BATCH REACTIONS)

| | | | | | | |
|---|---|---|---|---|---|---|
| 7 | 4/150 | 63.5 | 36.5 | 45.7 | 17.7 | 2.58 |
| 8 | 4/150 | 67.1 | 32.9 | 48.7 | 18.4 | 2.65 |
| 9 | 4/180 | 78.0 | 22.0 | 51.1 | 26.9 | 1.90 |
| 10 | 4/150 | 45.6 | 54.4 | 33.7 | 11.8 | 2.86 |
| 11 | 16/120 | 8.4 | 91.6 | 8.4 | ~0 | — |
| 12 | 3/150 | 78.6 | 21.4 | 48.6 | 30.0 | 1.62 |
| 13 | 6/180 | 78.1 | 21.9 | 48.9 | 29.3 | 1.67 |
| 14 | 7/180 | 63.5 | 36.5 | 48.7 | 24.8 | 1.96 |
| 15 | 6/150 | 78.9 | 21.1 | 47.6 | 31.4 | 1.52 |

Con. = Conversion;
M = Monomer;
D = Dimer;
T+ = Trimer + Tetramer+ etc.
A = Alpha;
I = Internal

TABLE II
PROPERTIES OF HYDROGENATED OLIGOMER FROM BATCH NO. 6 (TABLE I)

| | |
|---|---|
| Monomer | 1.69% |
| Dimer | 58.5% |
| Trimer | 29.6% |
| Tetramer | 9.53% |
| Pentamer | 0.76% |
| Pour Point (°F.) | −30 |
| Viscosity | 39.4 cSt (25° F.) |
| | 24.4 cSt (100° F.) |
| | 4.69 cSt (210° F.) |
| Viscosity Index | 125 |
| % Remaining by Thermogravimetric Analysis | |
| (233° C.) | 90.5% |
| (250° C.) | 83.5% |

EXAMPLE II

The following tables demonstrate the use of the present invention in continuous reaction systems. The 100 cc reactor (see Table III) was a 29"×0.62" stainless steel tube. The catalyst bed was about 100 cc. Liquid feed was pumped through the bottom of the reactor with a Ruska pump. A Uni-flow valve and a Foxboro controller were used to regulate pressure. The reactor was electrically heated. The 300 cc reactor (see Table IV) was a 29"×0.90" stainless steel tube. The catalyst bed was about 300 cc. Other equipment was the same as described regarding the 100 cc reactor.

TABLE III
C-12 ALPHA-OLEFIN OLIGOMERIZATION USING H/F CLAY-24 IN 100 cc CONTINUOUS REACTOR

| Sample No. | Liquid Flow (cc/Hr) | Temp. (C.) | Reactor Press. (psig) | Time Since Prior Sample (Hrs) | C (%) | M (%) | D (%) | T+ (%) | D/T+ Ratio |
|---|---|---|---|---|---|---|---|---|---|
| 1 | 18 | 150 | 200 | 4 | 75.5 | 24.5 | 43.9 | 31.6 | 1.39 |
| 2 | 18 | 156 | 200 | 6 | 82.4 | 17.6 | 41.6 | 40.8 | 1.02 |
| 3 | 18 | 169 | 300 | 17 | 80.5 | 19.5 | 42.4 | 38.1 | 1.11 |
| 4 | 18 | 200 | 300 | 6 | 73.2 | 26.8 | 44.5 | 28.7 | 1.55 |
| 5 | 20 | 200 | 300 | 16 | 77.1 | 22.9 | 52.0 | 25.1 | 2.07 |
| 6 | 20 | 150 | 300 | 6 | 69.4 | 30.6 | 46.5 | 22.9 | 2.03 |
| 7 | 20 | 149 | 300 | 15 | 64.1 | 35.9 | 46.5 | 12.6 | 2.64 |
| 8 | 20 | 149 | 300 | 4 | 61.9 | 38.1 | 42.3 | 14.6 | 3.28 |
| 9 | 20 | 155 | 300 | 4 | 48.1 | 51.9 | 32.5 | 15.6 | 2.08 |
| 10 | 20 | 156 | 300 | 4 | 54.0 | 58.4 | 35.0 | 19.0 | 1.84 |
| 11 | 20 | 156 | 300 | 15 | 58.4 | 41.6 | 39.8 | 18.7 | 2.13 |
| 12 | 20 | 155 | 300 | 9 | 59.2 | 40.8 | 40.2 | 19.0 | 2.12 |
| 13 | 20 | 155 | 300 | 14 | 62.8 | 37.2 | 41.8 | 21.0 | 1.99 |
| 14 | 20 | 155 | 300 | 7 | 65.8 | 34.2 | 41.8 | 24.0 | 1.24 |
| 15 | 20 | 155 | 300 | 15 | 67.5 | 32.5 | 42.4 | 25.1 | 1.69 |
| 16 | 20 | 155 | 300 | 4 | 65.0 | 35.0 | 43.9 | 21.2 | 2.08 |
| 17 | 20 | 153 | 300 | 15 | 68.8 | 31.2 | 45.7 | 34.1 | 1.98 |
| 18 | 20 | 156 | 300 | 9 | 73.7 | 26.3 | 48.3 | 25.4 | 1.90 |
| 19 | 20 | 156 | 300 | 15 | 77.2 | 22.8 | 47.4 | 29.8 | 1.59 |
| 20 | 20 | 156 | 300 | 15 | 77.2 | 22.8 | 47.4 | 29.8 | 1.59 |
| 21 | 20 | 156 | 300 | 16 | 72.3 | 22.7 | 49.3 | 28.0 | 1.76 |
| 22 | 20 | 156 | 300 | 24 | 74.4 | 25.6 | 48.6 | 25.8 | 1.89 |
| 23 | 20 | 156 | 300 | 8 | 72.4 | 27.6 | 49.6 | 22.8 | 2.18 |
| 24 | 20 | 156 | 300 | 16 | 71.1 | 8.9 | 48.0 | 23.2 | 2.07 |
| 25 | 20 | 156 | 300 | 24 | 68.1 | 31.9 | 32.3 | 20.7 | 2.28 |
| 26 | 20 | 158 | 300 | 9 | 66.4 | 33.6 | 46.8 | 19.6 | 2.39 |
| 27 | 20 | 156 | 300 | 24 | 66.5 | 33.3 | 46.2 | 20.3 | 2.27 |
| 28 | 20 | 156 | 300 | 15 | 64.1 | 35.9 | 46.4 | 12.9 | 2.62 |
| 29 | 20 | 156 | 300 | 9 | 64.1 | 39.9 | 44.1 | 20.0 | 2.21 |
| 30 | 20 | 156 | 300 | 15 | 62.4 | 37.6 | 48.1 | 18.4 | 2.40 |
| 31 | 20 | 156 | 300 | 9 | — | — | — | — | — |
| 32 | 20 | 153 | 300 | 15 | — | — | — | — | — |
| 33 | 20 | 155 | 300 | 9 | 57.9 | 42.1 | 41.8 | 16:7 | 2.46 |

TABLE III-continued

C-12 ALPHA-OLEFIN OLIGOMERIZATION USING H/F CLAY-24 IN 100 cc CONTINUOUS REACTOR

| Sample No. | Liquid Flow (cc/Hr) | Temp. (C.) | Reactor Press. (psig) | Time Since Prior Sample (Hrs) | C (%) | M (%) | D (%) | T+ (%) | D/T+ Ratio |
|---|---|---|---|---|---|---|---|---|---|
| 34 | 20 | 154 | 154 | 15 | 56.6 | 43.4 | 42.2 | 16.4 | 2.93 |

Distillation of Oligomers Prepared from C-12 Alpha-Olefin

Fractions from a $C_{12}$ run described in Table III were combined to give 1741 grams of product, which had the following analysis by liquid chromatography:

| | |
|---|---|
| Monomer | 27.8% |
| Dimer | 48.0% |
| Trimer | 19.3% |
| Tetramer | 4.91% |

This material was vacuum distilled through a one-foot Goodloe packed column until a pot temperature of 236° C. was reached. Four fractions were collected. The fourth fraction, boiling point 165°–170° C., at 0.8 mm HG, was 93.4% $C_{12}$ dimer. The pot residue was free of dimer and monomer. The reduced stripped dimer had the following properties:

| | |
|---|---|
| Viscosity (210° F.) | 2.50 cSt |
| Viscosity Index | 78.5 |
| Pour Point (°F.) | <−50 |
| % Remaining by TGA | |
| 233° C. | 30% |
| 250° C. | 1% |

The reduced pot residue had the following properties:

| | |
|---|---|
| Viscosity (210° F.) | 8.40 cSt |
| Viscosity Index | 128 |
| Pour Point (°F.) | −20 |
| % Remaining by TGA | |
| 233° C. | 99% |
| 250° C. | 98% |

TABLE IV

INTERNAL-OLEFIN[1] OLIGOMERIZATION USING H/F CLAY-24 IN 300 cc CONTINUOUS REACTOR

| Sample No. | Liquid Flow (cc/Hr) | Temp. (°C.) | Reactor Press. (psig) | Time Since Prior Sample (Hr.) | C (%) | M (%) | D (%) | T+ (%) | D/T+ Ratio |
|---|---|---|---|---|---|---|---|---|---|
| 1 | 48 | 150/155 | 300 | 3 | 5.4 | 94.5 | 5.1 | 0.4 | 12.8 |
| 2 | 48 | 151/158 | 300 | 15 | 32.4 | 67.6 | 24.0 | 8.4 | 2.86 |
| 3 | 48 | 151/158 | 300 | 4 | 64.3 | 35.7 | 39.3 | 25.0 | 1.57 |
| 4 | 48 | 151/157 | 300 | 5 | 59.1 | 40.9 | 44.4 | 14.7 | 3.02 |
| 5 | 48 | 152/157 | 300 | 15 | 58.6 | 41.4 | 44.6 | 14.1 | 3.16 |
| 6 | 48 | 148/153 | 300 | 25 | 64.4 | 35.6 | 47.6 | 16.7 | 2.85 |
| 7 | 48 | 149/155 | 300 | 8 | 68.1 | 32.0 | 43.9 | 19.4 | 2.26 |
| 8 | 48 | 146/154 | 300 | 15 | 65.2 | 34.8 | 48.3 | 16.9 | 2.86 |
| 9 | 48 | 148/152 | 300 | 9 | 68.6 | 31.5 | 45.1 | 23.4 | 1.93 |
| 10 | 48 | 143/152 | 300 | 4 | 62.4 | 37.6 | 42.7 | 19.8 | 2.16 |
| 11 | 48 | 143/152 | 300 | 19 | 62.0 | 38.0 | 43.1 | 19.0 | 2.27 |
| 12 | 48 | 141/150 | 300 | 5 | 61.5 | 38.5 | 43.6 | 17.9 | 2.44 |
| 13 | 48 | 141/150 | 300 | 4 | 63.1 | 36.9 | 43.9 | 19.2 | 2.29 |
| 14 | 48 | 143/152 | 300 | 15 | 62.7 | 37.3 | 43.5 | 19.1 | 2.28 |
| 15 | 48 | 145/153 | 300 | 9 | 60.1 | 39.9 | 46.7 | 23.4 | 2.00 |
| 16 | 48 | 147/157 | 300 | 16 | 59.2 | 40.8 | 45.2 | 14.0 | 3.23 |
| 17 | 48 | 147/156 | 300 | 8 | 63.4 | 36.6 | 44.6 | 18.8 | 2.37 |
| 18 | 48 | 147/156 | 300 | 15 | 60.2 | 39.9 | 46.6 | 13.5 | 3.45 |
| 19 | 48 | 151/159 | 300 | 9 | 59.2 | 40.8 | 46.1 | 13.1 | 3.52 |
| 20 | 48 | 151/159 | 300 | 15 | 55.4 | 44.6 | 44.1 | 11.4 | 3.89 |
| 21 | 48 | 151/159 | 300 | 3 | 56.3 | 43.7 | 39.9 | 16.2 | 2.46 |
| 22 | 48 | 144/155 | 300 | 15 | 47.7 | 52.3 | 38.7 | 8.96 | 4.32 |
| 23 | 48 | 145/155 | 300 | 9 | 48.0 | 52.0 | 39.0 | 9.00 | 4.33 |
| 24 | 48 | 145/155 | 300 | 15 | 43.9 | 56.1 | 35.2 | 8.69 | 4.05 |
| 25 | 48 | 147/156 | 300 | 9 | 39.7 | 60.4 | 32.5 | 2.13 | 4.56 |
| 26 | 48 | 147/156 | 300 | 15 | 41.0 | 59.0 | 33.3 | 2.32 | 4.31 |
| 27 | 48 | 139/155 | 300 | 4 | 25.6 | 24.4 | 20.7 | 4.93 | 4.20 |
| 28 | 48 | 145/155 | 300 | 15 | 39.5 | 60.5 | 31.0 | 8.43 | 3.68 |
| 29 | 48 | 146/155 | 300 | 4 | 35.9 | 64.1 | 30.2 | 5.74 | 5.26 |
| 30 | 48 | 146/155 | 300 | 17 | 32.2 | 67.8 | 26.8 | 5.43 | 4.94 |
| 31 | 48 | 146/155 | 300 | 9 | 29.9 | 70.1 | 24.3 | 5.64 | 4.31 |
| 32 | 56 | 146/155 | 300 | 15 | 28.0 | 72.0 | 23.5 | 4.59 | 5.12 |
| 33 | 50 | 148/158 | 300 | 9 | 26.0 | 74.0 | 21.8 | 4.22 | 5.17 |
| 34 | 50 | 148/158 | 300 | 15 | 27.6 | 78.4 | 23.1 | 4.55 | 5.08 |
| 35 | 50 | 148/158 | 300 | 9 | 28.8 | 71.2 | 23.7 | 5.09 | 4.66 |

Shell Chemical Co. Neoden ® 1518 IO: 1.8% $C_{14}$ and lower; 25.3% $C_{15}$; 26.3% $C_{16}$; 24.2% $C_{17}$; 18.5% $C_{18}$; and 3.9% $C_{19}$.

Distillation of Oligomers Prepared from Neodene ® 1518 IO

Samples 2, 5, 6, 7, and 8 from Table IV were combined to yield a total of 2600 grams of material, which had the following analysis by liquid chromatography:

| | |
|---|---|
| Monomer | 37.8% |
| Dimer | 40.2% |
| Trimer | 17.8% |
| Tetramer | 4.08% |

The material was placed in a five-liter flask and distilled through a one-foot Goodloe packed column until a pot temperature of 270° C. was reached (0.8 mm Hg). The pot residue (976 grams) was reduced with hydrogen and a nickel catalyst (5 wt. % catalyst, 200° C., 4.0 hours, 2000 psig hydrogen). The material obtained after filtration had the following properties:

| | |
|---|---|
| Viscosity (210° F.) | 8.40 cSt |
| Viscosity Index | 128 |
| % Remaining by TGA | |
| 233° C. | 99% |
| 250° C. | 98% |

EXAMPLE III

This example demonstrates the superior results obtained when the clays of the present invention are heat treated prior to oligomerizing the olefin.

Filtrol Clay-124 (200 grams) was placed in a vacuum and heat treated overnight for 20 hours at approximately 160° C. and a pressure of approximately 20 mm Hg. Before being heat treated, the clay had a moisture content of 7.11 wt. %. After being heat treated, the clay's moisture content was 1.03 wt. %. Results obtained when the heat treated clay was used to catalyze the oligomerization are shown in Table V, below. Table VI is offered for comparison.

TABLE V

C-14 ALPHA-OLEFIN OLIGOMERIZATION USING HEAT TREATED H/F CLAY-124 IN 100 cc CONTINUOUS REACTOR

| Sample No. | Liquid Flow (cc/Hr) | Temp (°C.) | Reactor Press (cc/Hr) | Time Since Prior Sample | Total Time | C (%) | M (%) | D (%) | T (%) | D/T + Ratio |
|---|---|---|---|---|---|---|---|---|---|---|
| 1 | 16 | 153 | 300 | 63 | (63) | 76.0 | 24.0 | 50.1 | 25.9 | 1.93 |
| 2 | 16 | 155 | 300 | 9 | (72) | 44.0 | 56.0 | 32.1 | 11.9 | 2.70 |
| 3 | 16 | 155 | 300 | 15 | (87) | 80.4 | 19.6 | 50.5 | 29.8 | 1.69 |
| 4 | 19 | 155 | 300 | 9 | (96) | 80.1 | 19.9 | 50.7 | 29.3 | 1.73 |
| 5 | 19 | 156 | 300 | 15 | (11) | 80.3 | 19.7 | 51.3 | 29.0 | 1.77 |
| 6 | 19 | 156 | 300 | 9 | (120) | 82.1 | 17.9 | 42.4 | 34.8 | 1.36 |
| 7 | 19 | 156 | 300 | 15 | (135) | 81.6 | 18.4 | 48.1 | 33.4 | 1.44 |
| 8 | 19 | 156 | 300 | 8 | (143) | 81.6 | 18.4 | 49.2 | 32.4 | 1.52 |
| 9 | 19 | 156 | 300 | 16 | (159) | 81.1 | 18.9 | 49.8 | 31.3 | 1.59 |
| 10 | 19 | 156 | 300 | 9 | (168) | 80.2 | 19.8 | 49.2 | 31.0 | 1.59 |
| 11 | 19 | 156 | 300 | 63 | (231) | 81.2 | 18.8 | 49.9 | 31.2 | 1.60 |
| 12 | 19 | 156 | 300 | 9 | (240) | 79.9 | 20.3 | 52.5 | 27.2 | 1.93 |
| 13 | 19 | 156 | 300 | 15 | (255) | 78.4 | 21.6 | 55.9 | 22.4 | 2.49 |
| 14 | 19 | 156 | 300 | 9 | (264) | 78.0 | 22.0 | 55.8 | 22.2 | 2.51 |
| 15 | 16 | 156 | 300 | 15 | (279) | 79.0 | 21.0 | 58.2 | 25.8 | 2.06 |
| 16 | 16 | 156 | 300 | 9 | (288) | 72.5 | 22.5 | 56.1 | 21.5 | 2.61 |
| 17 | 20 | 156 | 300 | 15 | (303) | 79.0 | 21.0 | 51.6 | 22.4 | 1.88 |
| 18 | 20 | 156 | 300 | 9 | (312) | 72.9 | 22.1 | 52.3 | 25.8 | 2.03 |
| 19 | 20 | 156 | 300 | 15 | (327) | 76.9 | 23.1 | 52.4 | 24.5 | 2.14 |
| 20 | 20 | 156 | 300 | 9 | (336) | 75.5 | 24.5 | 52.5 | 23.3 | 2.24 |
| 21 | 20 | 156 | 300 | 63 | (399) | 73.5 | 26.4 | 51.9 | 21.7 | 2.39 |
| 22 | 20 | 156 | | 9 | (408) | 68.7 | 31.1 | 51.0 | 17.7 | 2.88 |

TABLE VI

C-14 ALPHA-OLEFIN OLIGOMERIZATION USING NON-HEAT TREATED H/F CLAY-124 IN 100 cc CONTINUOUS REACTOR

| Sample No. | Liquid Flow (cc/Hr) | Temp (°C.) | React. Press. (cc/Hr) | Time Since Prior Sample | Total Time | C (%) | M (%) | D (%) | T (%) | D/T + Ratio |
|---|---|---|---|---|---|---|---|---|---|---|
| 1 | 20 | 155 | 300 | 8 | 8 | 73.5 | 26.5 | 47.1 | 26.3 | 1.75 |
| 2 | 20 | 155 | 300 | 14 | 14 | 77.1 | 22.9 | 46.8 | 30.5 | 1.53 |
| 3 | 20 | 155 | 300 | 8 | 30 | 77.3 | 22.7 | 48.0 | 28.3 | 1.71 |
| 4 | 20 | 155 | 300 | 16 | 46 | 78.8 | 21.1 | 48.1 | 29.6 | 1.63 |
| 5 | 20 | 155 | 300 | 8 | 54 | 79.8 | 20.2 | 48.3 | 31.5 | 1.53 |
| 6 | 20 | 155 | 300 | 15 | 69 | 79.9 | 20.1 | 47.1 | 32.8 | 1.44 |
| 7 | 20 | 155 | 300 | 9 | 78 | 79.6 | 20.4 | 47.6 | 32.0 | 1.49 |
| 8 | 20 | 155 | 300 | 63 | 141 | 78.2 | 21.3 | 49.9 | 28.5 | 1.75 |
| 9 | 20 | 155 | 300 | 9 | 150 | 77.2 | 22.8 | 51.2 | 26.1 | 1.96 |
| 10 | 20 | 155 | 300 | 15 | 165 | 75.9 | 24.2 | 51.6 | 24.2 | 2.13 |
| 11 | 20 | 156 | 300 | 9 | 174 | 73.7 | 26.3 | 52.7 | 21.0 | 2.51 |
| 12 | 20 | 156 | 300 | 15 | 189 | 78.9 | 27.1 | 50.0 | 22.9 | 2.18 |
| 13 | 20 | 156 | 300 | 9 | 198 | 72.8 | 27.7 | 49.9 | 22.4 | 2.23 |
| 14 | 20 | 156 | 300 | 15 | 213 | 71.7 | 28.3 | 49.9 | 22.2 | 2.25 |
| 15 | 20 | 156 | 300 | 9 | 222 | 70.5 | 29.5 | 50.3 | 20.2 | 2.49 |
| 16 | 20 | 154 | 300 | 15 | 232 | 70.1 | 29.9 | 49.9 | 20.2 | 2.47 |

TABLE VI-continued

C-14 ALPHA-OLEFIN OLIGOMERIZATION USING NON-HEAT TREATED H/F CLAY-124 IN 100 cc CONTINUOUS REACTOR

| Sample No. | Liquid Flow (cc/Hr) | Temp (°C.) | React. Press. (cc/Hr) | Time Since Prior Sample | Total Time | C (%) | M (%) | D (%) | T (%) | D/T + Ratio |
|---|---|---|---|---|---|---|---|---|---|---|
| 17 | 24 | 155 | 300 | 7 | 244 | 62.2 | 32.8 | 47.3 | 19.9 | 2.38 |
| 18 | 24 | 155 | 300 | 65 | 309 | 62.2 | 37.7 | 45.5 | 16.8 | 2.71 |
| 19 | 24 | 155 | 300 | 90 | 318 | 59.1 | 40.9 | 43.9 | 15.2 | 2.89 |
| 20 | 24 | 155 | 300 | 15 | 333 | 56.8 | 43.2 | 44.0 | 22.7 | 1.94 |
| 21 | 24 | 155 | 300 | 9 | 342 | 56.5 | 43.5 | 41.8 | 14.7 | 2.84 |
| 22 | 24 | 155 | 300 | 15 | 357 | 54.1 | 45.9 | 42.5 | 11.6 | 2.66 |
| 23 | 24 | 155 | 300 | 9 | 366 | 52.0 | 48.0 | 40.7 | 11.2 | 3.57 |
| 24 | 24 | 155 | 300 | 15 | 381 | 50.7 | 49.3 | 40.1 | 10.6 | 3.78 |
| 25 | 24 | 155 | 300 | 9 | 390 | 49.6 | 50.4 | 38.1 | 11.5 | 3.31 |
| 26 | 24 | 155 | 300 | 15 | 405 | 50.2 | 49.8 | 32.9 | 12.4 | 3.06 |
| 27 | 24 | 154 | 300 | 9 | 414 | 47.3 | 52.7 | 37.8 | 9.47 | 3.99 |
| 28 | 24 | 154 | 300 | 63 | 417 | 48.2 | 51.8 | 32.8 | 10.4 | 3.63 |
| 29 | 24 | 155 | 300 | 9 | 486 | 51.4 | 48.6 | 34.6 | 7.17 | 4.83 |
| 30 | 24 | 155 | 300 | 15 | 501 | 49.4 | 50.6 | 37.1 | 12.3 | 3.02 |
| 31 | 19 | 155 | 300 | 9 | 510 | 45.8 | 54.2 | 36.7 | 9.10 | 4.03 |
| 32 | 20 | 155 | 300 | 15 | 525 | 45.5 | 54.4 | 36.1 | 9.38 | 3.85 |
| 33 | 20 | 155 | 300 | 9 | 534 | 44.9 | 55.1 | 35.6 | 8.21 | 4.47 |
| 34 | 20 | 155 | 300 | 15 | 549 | 43.5 | 56.3 | 36.7 | 7.89 | 4.51 |
| 35 | 20 | 155 | 300 | 8 | 557 | 42.3 | 57.7 | 34.3 | 7.94 | 4.32 |
| 36 | 19 | 155 | 300 | 16 | 573 | 41.4 | 58.6 | 34.2 | 7.28 | 4.65 |
| 37 | 19 | 155 | 300 | 9 | 582 | 39.2 | 60.8 | 32.4 | 6.80 | 4.76 |
| 38 | 19 | 155 | 300 | 63 | 645 | 38.7 | 61.3 | 31.8 | 6.93 | 4.59 |
| 39 | 19 | 155 | 300 | 9 | 654 | 44.1 | 55.9 | 35.5 | 8.57 | 4.14 |
| 40 | 19 | | | 15 | 661 | 37.5 | 62.5 | 30.7 | 6.75 | 4.55 |

In Tables V and VI above, conversion of $C_{14}$ alpha-olefin versus time is shown for heat treated Harshaw/Filtrol Clay 124 (1.0 wt. % $H_2O$) and non-heat treated Clay 124 (7.1 wt. % $H_2O$), respectively. The reaction conditions for both continuous reactions were 155° C., 300 psig, and an LHSV (Liquid Hourly Space Velocity) of .2. Table V demonstrates the increased activity and prolonged catalyst life achieved by heat treating the clay prior to its use as a catalyst, showing about 80 to 82% conversion at 90 to 230 hours, and 72 to 79% conversion from 250 to 400 hours, total continuous reaction time. Table VI, on the other hand, shows that the non-heat treated clay was less active at peak activity (achieving 70 to 79% conversion), and that its activity decreased more rapidly (conversion dropped to 62 % and then to below 50% by 400 hours, total continuous reaction time.)

We claim:

1. A process for the preparation of oligomers, comprising contacting a linear olefin containing from 10 to 24 carbon atoms with a catalytically effective amount of an acidic calcium montmorillonite clay having a moisture content ranging up to about 20 wt. %, a residual acidity in the range of about 3 to about 30 mg KOH/g, and a surface area of about 300 $M^2/g$ or greater.

2. The process of claim 1, wherein the moisture content of the clay is about 12 wt. %, the residual acidity is about 8.5 mg KOH/g, and the surface area is about 425 $M^2/g$.

3. The process of claim 1, wherein the moisture content of the clay is about 2 wt. %, the residual acidity is about 7.0 mg KOH/g, and the surface area is about 400 $M^2/g$.

4. The process of claim 1, wherein the moisture content of the clay is about 16 wt. %, the residual acidity is about 15 mg KOH/g, and the surface area is about 300 $M^2/g$.

5. The process of claim 1, wherein the moisture content of the clay is about 4 wt. %, the residual acidity is about 10 mg KOH/g, and the surface area is about 300 $M^2/g$.

6. The process of claim 1, wherein the moisture content of the clay is essentially nil, the residual acidity is about 3.0 mg KOH/g, and the surface area is about 350 $M^2/g$.

7. The process of claim 1, wherein the olefin is contacted with the clay at a temperature of about 150° to about 180° C.

8. A process for the preparation of oligomers, comprising contacting a linear olefin containing from 12 to 18 carbon atoms with a catalytically effective amount of an acidic calcium montmorillonite clay having a moisture content ranging up to about 20 wt. %, a residual acidity in the range of about 3 to about 30 mg KOH/g, and a surface area of about 300 $M^2/g$ or greater.

9. The process of claim 8, wherein the moisture content of the clay is about 12 wt. %, the residual acidity is about 8.5 mg KOH/g, and the surface area is about 425 $M^2/g$.

10. The process of claim 8, wherein the moisture content of the clay is about 2 wt. %, the residual acidity is about 7.0 mg KOH/g, and the surface area is about 400 $M^2/g$.

11. The process of claim 8, wherein the moisture content of the clay is about 16 wt. %, the residual acidity is about 15 mg KOH/g, and the surface area is about 300 $M^2/g$.

12. The process of claim 8, wherein the moisture content of the clay is about 4 wt. %, the residual acidity is about 10 mg KOH/g, and the surface area is about 300 $M^2/g$.

13. The process of claim 8, wherein the moisture content of the clay is essentially nil, the residual acidity is about 3.0 mg KOH/g, and the surface area is about 350 $M^2/g$.

14. The process of claim 8, wherein the olefin is contacted with the clay at a temperature of about 150° to about 180° C.

15. The process of claim 8, wherein the olefin contains from 13 to 16 carbon atoms.

16. A process for the preparation of oligomers, comprising the following steps:
(a) heat treating to a moisture content of about 1 wt. % or less an acidic calcium montmorillonite clay having a moisture content prior to heat treatment ranging up to about 20 wt. % or less, having a residual acidity in the range of about 3 to about 30 mg KOH/g, and a surface area of about 300 $M^2/g$ or greater; and
(b) contacting a linear olefin containing from 10 to 24 carbon atoms with a catalytically effective amount of said clay.

17. The process of claim 16, wherein the moisture content of the clay prior to heat treatment is about 12 wt. %, the residual acidity is about 8.5 mg KOH/g, and the surface area is about 425 $M^2/g$.

18. The process of claim 16, wherein the moisture content of the clay prior to heat treatment is about 2 wt. %, the residual acidity is about 7.0 mg KOH/g, and the surface area is about 400 $M^2/g$.

19. The process of claim 16, wherein the moisture content of the clay prior to heat treatment is about 16 wt. %, the residual acidity is about 15 mg KOH/g, and the surface area is about 300 $M^2/g$.

20. The process of claim 16, wherein the moisture content of the clay prior to heat treatment is about 4 wt. %, the residual acidity is about 10 mg KOH/g, and the surface area is about 300 $M^2/g$.

21. The process of claim 16, wherein the moisture content of the clay prior to heat treatment is essentially nil, the residual acidity is about 3.0 mg KOH/g, and the surface area is about 350 $M^2/g$.

22. The process of claim 16, wherein the olefin is contacted with the clay at a temperature of about 150° to about 180° C.

23. The process of claim 16, wherein the temperature at which the clay is heat treated is from 50° to 350° C.

24. A process for the preparation of oligomers, comprising the following steps:
(a) drying to a moisture content of about 1 wt. % or less an acidic calcium montmorillonite clay having a moisture content prior to heat treatment ranging up to about 20 wt. % or less, a residual acidity in the range of about 3 to about 30 mg KOH/g, and a surface area of about 300 $M^2/g$ or greater; and
(b) contacting a liner olefin containing from 12 to 18 carbon atoms with a catalytically effective amount of said clay.

25. The process of claim 24, wherein the moisture content of the clay prior to heat treatment is about 12 wt. %, the residual acidity is about 8.5 mg KOH/g, and the surface area is about 425 $M^2/g$.

26. The process of claim 24, wherein the moisture content of the clay prior to heat treatment is about 2 wt. %, the residual acidity is about 7.0 mg KOH/g, and the surface area is about 400 $M^2/g$.

27. The process of claim 24, wherein the moisture content of the clay prior to heat treatment is about 16 wt. %, the residual acidity is about 15 mg KOH/g, and the surface area is about 300 $M^2/g$.

28. The process of claim 24, wherein the moisture content of the clay prior to heat treatment is about 4 wt. %, the residual acidity is about 10 mg KOH/g, and the surface area is about 300 $M^2/g$.

29. The process of claim 24, wherein the moisture content of the clay prior to heat treatment is essentially nil, the residual acidity is about 3.0 mg KOH/g, and the surface area is about 350 $M^2/g$.

30. The process of claim 24, wherein the olefin is contacted with the clay at a temperature of about 150° to about 180° C.

31. The process of claim 24, wherein the olefin contains from 13 to 16 carbon atoms.

32. The process of claim 24, wherein the temperature at which the clay is heat treated is from 50° to 350° C.

33. A process for preparing a synthetic lubricant component, comprising: oligomerizing a linear olefin having from 10 to 24 carbon atoms by contacting said olefin with a catalytically effective amount of an acidic calcium montmorillonite clay having a moisture content ranging up to about 20 wt. %, a residual acidity in the range of about 3 to about 30 mg KOH/g, and a surface area of about 300 $M^2/g$ or greater; separating out any remaining un-oligomerized olefin; and hydrogenerating the resulting oligomer fraction to produce a synthetic lubricant component.

34. The process of claim 33, wherein the olefin contains from 12 to 18 carbon atoms.

35. The process of claims 33 or 34, wherein, before being contacted with the olefin, the clay is heat treated to a moisture content of about 1 wt. % or less.

* * * * *